United States Patent [19]

Dravland

[11] Patent Number: 4,906,243
[45] Date of Patent: Mar. 6, 1990

[54] COMBINATION DIAPER AND TRAINING PANTS

[76] Inventor: Mary Dravland, 2611 Moeller Dr., Hamilton, Ohio 45014

[21] Appl. No.: 151,597

[22] Filed: Feb. 2, 1988

[51] Int. Cl.⁴ ............................................. A61F 13/16
[52] U.S. Cl. ................................... 604/394; 604/385.2
[58] Field of Search ............... 604/393, 394, 358, 378, 604/385.1, 385.2, 386, 387, 397, 400, 401

[56] References Cited

U.S. PATENT DOCUMENTS

| | | | |
|---|---|---|---|
| Re. 30,057 | 7/1979 | Schaar | 604/378 |
| D. 249,280 | 9/1978 | Banuelos | 604/385.1 |
| 1,971,671 | 8/1934 | Alsop | 604/397 |
| 2,141,105 | 12/1938 | Eller et al. | 604/394 |
| 2,290,110 | 7/1942 | McGraw | 604/385.1 |
| 2,577,398 | 12/1951 | Blake | 604/378 |
| 2,581,904 | 1/1952 | Burns | 604/394 |
| 2,638,899 | 5/1953 | Ambarian | 604/401 |
| 2,890,700 | 6/1959 | Lönberg-Holm | 604/378 |
| 2,898,912 | 8/1959 | Adams | 604/397 |
| 2,956,564 | 10/1960 | Ohara | 604/397 |
| 3,077,193 | 2/1963 | Mann | 604/401 |
| 3,530,859 | 9/1970 | Heimowitz | 604/378 |
| 3,744,494 | 7/1973 | Marsan | 604/385.1 |
| 3,776,232 | 12/1973 | Schaar | 604/385.1 |
| 3,776,233 | 12/1973 | Schaar | 604/385.1 |
| 3,860,004 | 1/1975 | Nystrand | 604/385.1 |
| 3,881,488 | 5/1975 | Delanty et al. | |
| 3,882,871 | 5/1975 | Taniguchi | 604/371 |
| 4,051,854 | 10/1977 | Aaron | 604/397 |
| 4,108,179 | 8/1978 | Schaar | 604/385.1 |
| 4,182,334 | 1/1980 | Johnson | 604/385.2 |
| 4,300,563 | 11/1981 | Brookfield | 604/385.1 |
| 4,315,508 | 2/1982 | Bolick | 604/385.2 |
| 4,516,975 | 5/1985 | Mitchell | 604/385 |
| 4,573,987 | 3/1986 | Lamb, Jr. | 604/378 |
| 4,578,073 | 3/1986 | Dysart et al. | 604/385.2 |
| 4,596,568 | 6/1986 | Flug | 604/378 |
| 4,610,680 | 9/1986 | LaFleur | 604/385 |
| 4,610,682 | 9/1986 | Kopp | 604/385 |
| 4,615,695 | 10/1986 | Cooper | 604/385 |
| 4,619,649 | 10/1986 | Roberts | 604/385 |
| 4,642,819 | 2/1987 | Ales et al. | 604/385 |
| 4,671,793 | 6/1987 | Hults et al. | 604/385 |
| 4,704,116 | 11/1987 | Enloe | 604/385.2 |
| 4,731,070 | 3/1988 | Koci | 604/385.1 |

*Primary Examiner*—C. Fred Rosenbaum
*Assistant Examiner*—Sharon Rose

[57] ABSTRACT

A garment comprising combination diaper and training pants includes an outer layer formed of water impervious material, an inner liner formed of thin absorbent material, and a core formed of water absorbent material sandwiched between the outer layer and the inner liner. The garment has a back section, a front section and an intermediate section. The back section of the garment extends partially around the waist of a wearer and is fastened to the front section. The intermediate section of the garment is generally hourglass shaped with a special contour to cover the wearer's seat and crotch areas without excessive bulkiness in the crotch area while forming a pocket in the garment adjacent the seat area for collecting waste.

4 Claims, 2 Drawing Sheets

COMBINATION DIAPER AND TRAINING PANTS

BACKGROUND OF THE INVENTION

This invention relates generally to garments and, in particular, to an improved combination diaper and training pants which may be worn by children from birth through toilet training and by adults.

U.S. Pat. No. 4,615,695 to R. M. Cooper discloses a combination diaper training pant for children and adults which includes a water absorbent padding disposed between a water absorbing inner liner and a water resistant outer layer. Since the garment disclosed by Cooper is intended for universal use, it is often uncomfortable to the wearer. For example, the leg openings of the Cooper garment are not properly contoured and the crotch is too bulky. U.S. Pat. Nos. 4,516,975 to D. J. Mitchell and U.S. Pat. No. 4,573,987 to K. A. Lamb, Jr. disclose reusable diapers which are also uncomfortable to the wearer due to their improperly contoured leg openings and bulkiness in the crotch area. Conventional training pants must be removed by pulling them down on the wearer's body thus presenting the problem of solid waste leaking out.

SUMMARY OF THE INVENTION

It is an object of the present invention to provide an improved combination diaper and training pants which fits comfortably on the wearer but which may be quickly and easily removed from the wearer in the same manner as a diaper.

It is another object of the present invention to provide an improved combination diaper and training pants which has properly contoured leg openings and is less bulky in the crotch area of the wearer.

It is a further object of the present invention to provide an improved combination diaper and training pants which includes a pocket formed adjacent the seat area of the wearer for collecting waste without creating too much bulk.

Another object of the present invention is to provide an improved combination diaper and training pants having inverted V-shaped leg openings in the front allowing freer forward and upward movement of the legs of the wearer and less bulk under clothing.

The present invention accomplishes these objects by providing a garment comprising combination diaper and training pants including a back section of generally rectangular shape in plan view, a front section of generally rectangular shape in plan view, and an intermediate section of generally hourglass shape in plan view extending between the back and front sections. The back section extends around the waist of a wearer and is fastened to the front section. The intermediate section covers the seat and crotch areas of the wearer while forming a pocket in the garment adjacent the seat area of the wearer for collecting waste. The intermediate section of the garment has a first relatively large area in plan view adjoining the back section thereof and a second relatively small area in plan view adjoining the front section thereof. The first relatively large area is defined by radially convex side edges whereas the second relatively small area is defined by radially concave side edges.

In the preferred embodiment of the present invention, the combination diaper and training pants includes an outer layer formed of water impervious material, an inner liner formed of thin absorbent material, and a core formed of water absorbent material sandwiched between the outer layer and the inner liner. The outer layer and the inner liner both include back, front and intermediate portions corresponding in shape to the back, front and intermediate sections, respectively, of the garment. A first elastic strip extends across the back portion of the outer layer, and second and third elastic strips extend along the sides of the intermediate portion of the outer layer. The core includes a back portion of generally rectangular shape in plan view, a front portion of generally trapezoidal shape in plan view, and a contoured intermediate portion extending between the back and front portions thereof.

DESCRIPTION OF THE PREFERRED EMBODIMENT

Figure 1:
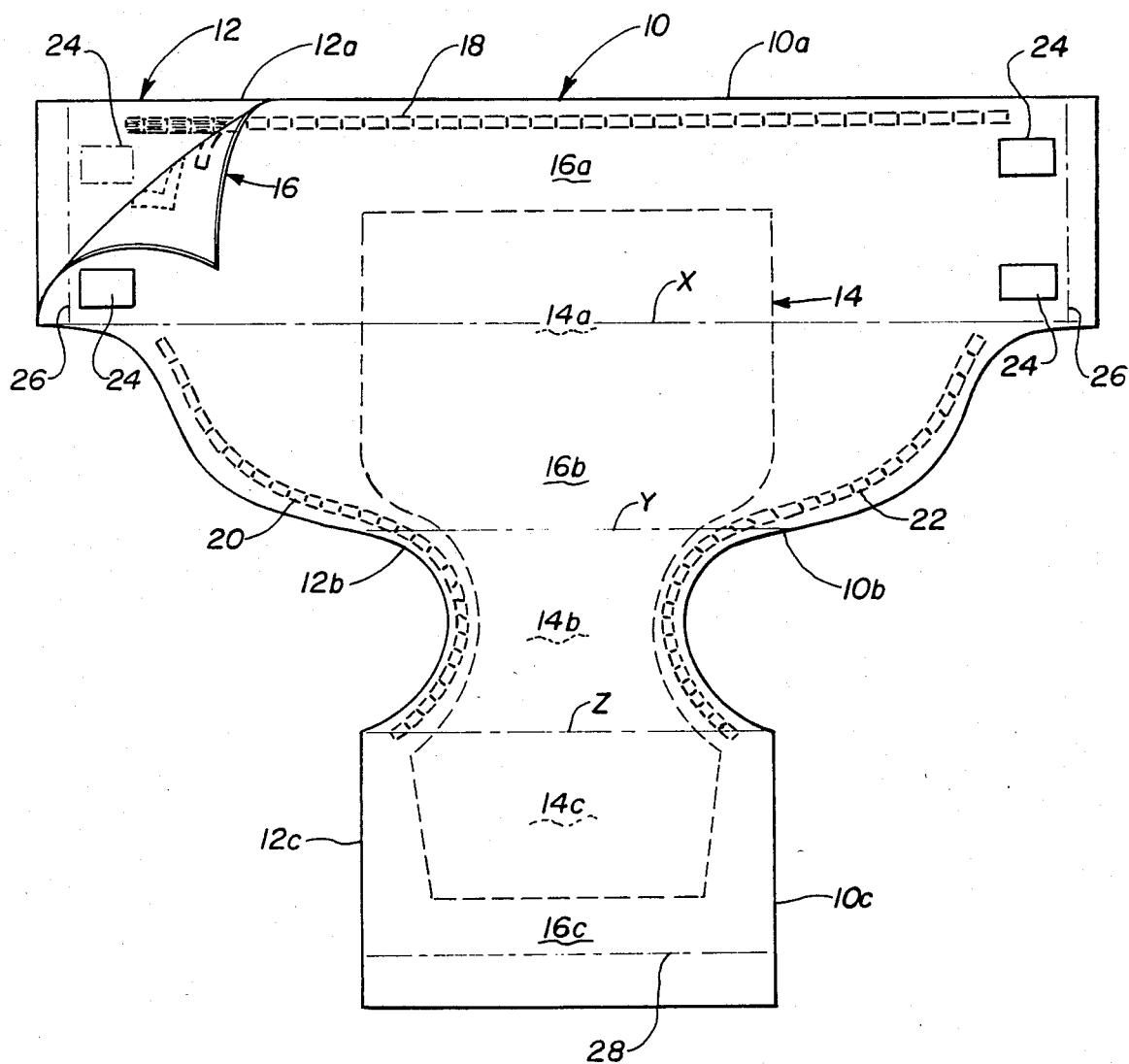
FIG. 1 is a plan view o a combination diaper and training pants according to the preferred embodiment of the present invention.
Figure 2:
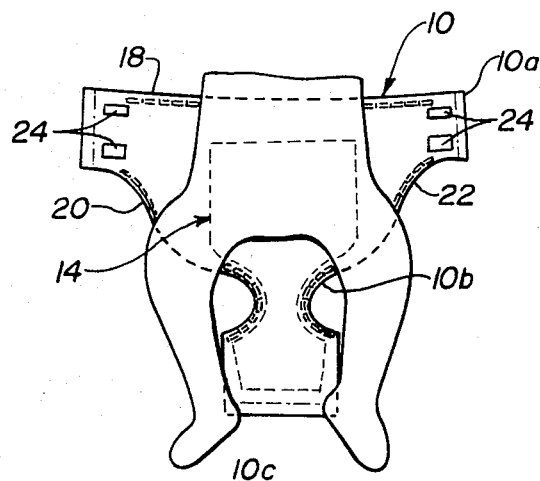
FIG. 2 is a schematic plan view of the combination diaper and training pants of FIG. 1 positioned underneath the body of an infant.
Figure 3:
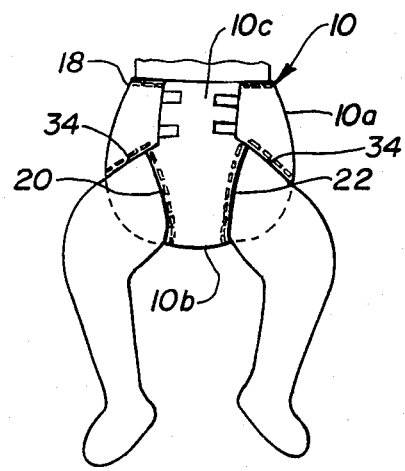
FIG. 3 is a schematic front view of the combination diaper and training pants of FIG. 1 after being secured on the body of an infant.

Referring to FIG. 1, a garment 10 comprising combination diaper and training pants according to the preferred embodiment of the present invention includes an outer layer 12, a core 14, and an inner liner 16. The outer layer 12 is formed of water impervious material, the core 14 is formed of water absorbent material, and the inner liner 16 is formed of thin absorbent material.

The garment 10 includes a back section 10a, an intermediate section 10b, and a front section 10c. In plan view as seen in FIG. 1, the back section 10a is generally rectangular in shape, the intermediate section 10b is generally hourglass shaped, and the front section 10c is generally rectangular in shape. The intermediate section 10b has a first relatively large area in plan view adjoining the back section 10a and a second relatively small area in plan view adjoining the front section 10c. As seen in FIG. 1, the first relatively large area of the intermediate section 10b lying between lines x and y is defined by radially convex side edges whereas the second relatively small area of the intermediate section 10b lying between lines y and z is defined by radially concave side edges.

The outer layer 12 has a back portion 12a, an intermediate portion 12b, and a front portion 12c corresponding in shape to the back section 10a, intermediate section 10b, and front section 10c, respectively, of the garment 10. The core 14 has a back portion 14a that is generally rectangular, a contoured intermediate portion 14b, and a front portion 14c that is generally trapezoidal shaped. The inner liner 16 has a back portion 16a, an intermediate portion 16b, and a front portion 16c which are identical in shape to the back portion 12a, the intermediate portion 12b and the front portion 12c, respectively, of the outer layer 12.

The garment 10 is assembled by utilizing conventional means such as double sided adhesive tape or glue to attach an elastic strip 18 across the back portion 12a of the outer layer 12 and to attach elastic strips 20, 22 along the side edges of the intermediate portion 12b of the outer layer 12. The elastic strips 20, 22 are stretched between the back and front portions 12a, 12c of the outer layer 12 thereby contracting and distorting the garment intermediate section 10b to create a pocket 30 (FIG. 4) for collecting liquid and solid waste and to also create a channel 32 (FIG. 4) for directing the flow of liquid waste into the pocket 30. The core 14 is then fastened to the outer layer 12 by conventional means such as double sided adhesive tape or glue. Finally, the inner layer 16 is secured to the outer layer 12 by suitable means so that the core 14 is sandwiched between the outer layer 12 and the inner liner 16. The garment 10 is completed by attaching tape tabs 24 to the back portion 16a of the inner liner 16 by providing fold lines 26, 28 on the outer layer 12 and the inner liner 16.

Figure 4:
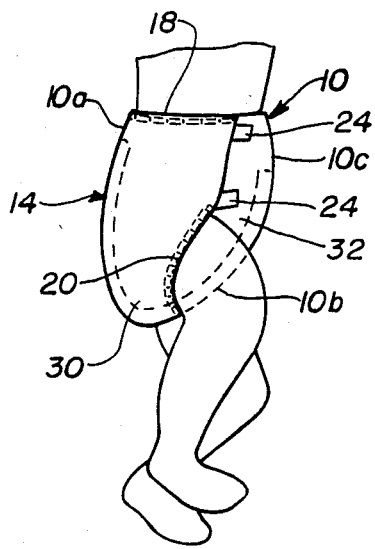
FIG. 4 is a schematic side view of the combination diaper and training pants of FIG. 1 after being secured on the body of an infant.
Figure 5:
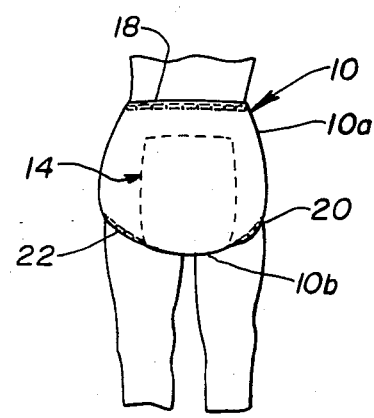
FIG. 5 is a schematic back view of the combination diaper and training pants of FIG. 1 after being secured on the body of an infant.

The manner in which the garment 10 is secured on the body of a wearer such as an infant is illustrated in FIGS. 2-5. The back seciton 10a extends partially around the infant's waist and the tape tabs 24 are extended to secure the back section 10a to the front section 10c. The intermediate section 10b covers the infant's seat and crotch areas, and the front section 10c partially covers the infant's abdominal area. The hourglass shaped contour of the intermediate section 10b results in less bulk between the infant's legs while the elastic strips 20, 22 contract and distort the intermediate section 10b thereby forming pocket 30 and channel 32 adjacent the seat and crotch areas, respectively, of the infant as seen in FIG. 4. The pocket 30 collects solid and liquid waste, and the channel 32 directs the flow of liquid waste into the pocket 30. The intermediate section 10b is also hourglass shaped shaped to provide inverted V-shaped leg openings 34 (FIG. 3) in the front allowing freer forward and upward movement of the infant's legs and less bulk under clothing.

Once the garment 10 is secured on the infant's body as shown in FIGS. 2-5, it may be slipped up and down with ease due to the elastic strips 18, 20, 22 to serve as training pants. The intermediate section 10b fits snugly around the infant's legs to prevent liquid waste from leaking out of the garment 10 while collecting liquid and solid waste in the pocket 30 which is formed adjacent the infant's seat area.

It will be understood that the garment 10 of the present invention may be made in different sizes to fit infants, toddlers and even adults. The garment 10 could also be constructed such that the core 14 may be removed when soiled and replaced with a new clean one.

The present invention thus provides combination diaper and training pants which fits comfortably on a wearer with properly contoured leg openings and less bulk in the wearer's crotch area.

While the preferred embodiment of the present invention has been disclosed herein, it will be understood that the following claims also cover other embodiments of the present invention.

What is claimed is:

1. A garment comprising combination diaper and training pants including a back section of generally rectangular shape in plan view, a front section of generally rectangular shape in plan view, an intermediate section of generally hourglass shape in plan view extending between said back and front sections, said back section extending around the waist of a wearer and being fastened to said front section, and said intermediate section covering the seat and crotch areas of the wearer while forming a pocket in the garment adjacent the seat area of the wearer for collecting waste;

said intermediate section having a first relatively large area in plan view adjoining said back portion and a second relatively small area in plan view adjoining said front section, said first relatively large area being defined by radially convex side edges, and said second relatively small area being defined by radially concave side edges;

said combination diaper and training pants including an outer layer formed of water impervious material, an inner liner formed of thin absorbent material, and a core formed of water absorbent material sandwiched between said outer layer and said inner liner;

said outer layer and said inner liner both including back, front and intermediate portions corresponding in shape to said back, front and intermediate sections, respectively, of the garment; and a first elastic strip extending across an upper edge of said back portion of said outer layer, and second and third elastic strips stretched along the opposite convex and concave side edges of said intermediate portion of said outer layer thereby contracting and distorting said intermediate section to form said pocket for collecting solid and liquid waste and to also form a channel adjacent the crotch area of the wearer for directing liquid waste into said pocket.

2. The garment of claim 1; wherein said core includes a back portion of generally rectangular shape in plan view, a front portion of generally trapezoidal shape in plan view, and a contoured intermediate portion extending between said back and front portions thereof.

3. The garment of claim 2, further comprising tape tabs mounted on said back portion of said inner liner for releasably fastening said back section of the garment to said front section thereof.

4. The garment of claim 1, wherein said core is removable and replaceable.

* * * * *